(12) United States Patent
Mansi et al.

(10) Patent No.: US 12,636,086 B2
(45) Date of Patent: May 26, 2026

(54) RISK MANAGEMENT FOR ROBOTIC CATHETER NAVIGATION SYSTEMS

(71) Applicant: SIEMENS HEALTHINEERS AG, Forchheim (DE)

(72) Inventors: Tommaso Mansi, Plainsboro, NJ (US); Young-Ho Kim, West Windsor, NJ (US); Rui Liao, Princeton Junction, NJ (US); Yue Zhang, Jersey City, NJ (US); Puneet Sharma, Princeton Junction, NJ (US); Dorin Comaniciu, Princeton, NJ (US)

(73) Assignee: Siemens Healthineers AG, Forchheim (DE)

( * ) Notice: Subject to any disclaimer, the term of this patent is extended or adjusted under 35 U.S.C. 154(b) by 1154 days.

(21) Appl. No.: 17/456,681

(22) Filed: Nov. 29, 2021

(65) Prior Publication Data

US 2023/0165638 A1 Jun. 1, 2023

(51) Int. Cl.
*A61B 34/20* (2016.01)
*G06T 7/11* (2017.01)

(52) U.S. Cl.
CPC ................ *A61B 34/20* (2016.02); *G06T 7/11* (2017.01); *A61B 2034/2065* (2016.02); *G06T 2207/20081* (2013.01); *G06T 2207/30101* (2013.01)

(58) Field of Classification Search
CPC .............. A61B 34/20; A61B 2034/301; G06T 2207/30101
See application file for complete search history.

(56) References Cited

U.S. PATENT DOCUMENTS 4,878,115 A 10/1989 Elion
10,169,875 B2 1/2019 Mintz et al.
(Continued)

FOREIGN PATENT DOCUMENTS

CN 104736085 A 6/2015
CN 108685560 A 10/2018
(Continued)

OTHER PUBLICATIONS

Abdelaziz et al., "Toward a Versatile Robotic Platform for Fluoroscopy and MRI-Guided Endovascular Interventions: A Pre-Clinical Study", 2019, IEEE. (Year: 2019).*
(Continued)

*Primary Examiner* — Anne M Kozak
*Assistant Examiner* — Kaitlyn Eunji Kim

(57) ABSTRACT

Systems and methods for navigating a catheter in a patient using a robotic navigation system with risk management are provided. An input medical image of a patient is received. A trajectory for navigating a catheter from a current position to a target position in the patient is determined based on the input medical image using a trained segmentation network. One or more actions of a robotic navigation system for navigating the catheter from the current position towards the target position and a confidence level associated with the one or more actions are determined by a trained AI (artificial intelligence) agent and based on the generated trajectory and a current view of the catheter. In response to the confidence level satisfying a threshold, the one or more actions are evaluated based on a view of the catheter when navigated according to the one or more actions. The catheter is navigated from the current position towards the target position using the robotic navigation system according to the one or more actions based on the evaluation.

20 Claims, 10 Drawing Sheets

(56) References Cited

U.S. PATENT DOCUMENTS

| | | | |
|---|---|---|---|
| 10,646,288 | B2 | 5/2020 | Yeung et al. |
| 10,888,248 | B2 | 1/2021 | Zhao et al. |
| 11,147,635 | B1 | 10/2021 | Sganga et al. |
| 11,229,493 | B2 | 1/2022 | Finley et al. |
| 12,334,224 | B2 | 6/2025 | Sharma et al. |
| 2004/0097805 | A1 | 5/2004 | Verard et al. |
| 2018/0296281 | A1* | 10/2018 | Yeung et al. .......... A61B 34/30 |
| 2019/0142520 | A1 | 5/2019 | VanDyken |
| 2020/0383734 | A1 | 12/2020 | Dahdouh et al. |
| 2021/0264589 | A1 | 8/2021 | Jacob et al. |
| 2021/0319556 | A1* | 10/2021 | Chauhan |

FOREIGN PATENT DOCUMENTS

| | | |
|---|---|---|
| CN | 108778113 A | 11/2018 |
| CN | 113316430 A | 8/2021 |
| CN | 113538327 A | 10/2021 |
| WO | 2021008697 A1 | 1/2021 |

OTHER PUBLICATIONS

Yang et al., "Catherer-based photoacoustic endoscope", 2014, J Biomed Optics, vol. 19, Issue 6 (Year: 2014).*

Luca, "Surgical Path Planner for Steerable Catheters with Reinforcement Learning Approach", 2018, Politecnico di Milano (Year: 2018).*

Fu et al., "Rapid vessel segmentation and reconstruction of head and neck angiograms using 3D convolutional neural network", 2020, Nature Communications, 11, Article 4829 (Year: 2020).*

Wang et al., Wang et al., "Annotation-efficient deep learning for automatic medical image segmentation", 2021, Nature Communications, Article 5915 (Year: 2021).*

Favaro et al., "Automatic optimized 3D path planner for steerable catheters with heuristic search and uncertainty tolerance", 2018, 2018 IEEE International Conference on Robotics and Automation (Year: 2018).*

Juabert et al., "Real-time deep artifact suppression using recurrent U-Nets for low-latency cardiac MRI", 2020, Magnetic Resonance in Medicine, 86(4):1904-1916 (Year: 2020).*

Piayda et al., "Dynamic coronary roadmapping during percutaneous coronary intervention: a feasibility study," European journal of medical research, 2018, vol. 23, No. 1, pp. 1-7.

Ma et al., "Dynamic coronary roadmapping via catheter tip tracking in x-ray fluoroscopy with deep learning based bayesian Itering," Medical image analysis, 2020, vol. 61, pp. 1-29.

Ronneberger et al., "U-net: Convolutional networks for biomedical image segmentation," in International Conference on Medical image computing and computer-assisted intervention. Springer, 2015, pp. 234-241.

Long et al., "Fully convolutional networks for semantic segmentation," in Proceedings of the IEEE conference on computer vision and pattern recognition, 2015, pp. 3431-3440.

Bonalli et al., "Gusto: Guaranteed sequential trajectory optimization via sequential convex programming," in 2019 International Conference on Robotics and Automation (ICRA), IEEE, 2019, pp. 6741-6747.

Schulman et al., Motion planning with sequential convex optimization and convex collision checking, The International Journal of Robotics Research, vol. 33, No. 9, 2014, pp. 1251-1270.

Amersfoort et al., "Improving deterministic uncertainty estimation in deep learning for classication and regression," arXiv preprint arXiv:2102.11409, 2021.

Li et al., "Investigation of guidewire deformation in blood vessels based on an sqp algorithm," Applied Sciences, vol. 9, No. 2, 2019, pp. 1-17.

Auris, "MONARCH Endoscopy Transformed", https://www.aurishealth.com/monarch-platform, retrieved online on Sep. 2, 2021, 7 pgs.

Intuitive, "Ion by Intuitive, A robotic-assisted endoluminal platform for minimally invasive peripheral lung biopgy", https://www.intuitive.com/en-us/products-and-services/ion, retrieved online on Sep. 2, 2021, 6 pgs.

Corindus, https://www.corindus.com, retrieved online on Sep. 2, 2021, 3 pgs.

Tsui, "Versatile Robotic Platform for Fluoroscopy & MRI-Guided Endovascular Intervention," 2021, Imperial College London, https://www.imperial.ac.uk/news/195513/versatile-robotic-platform-fluoroscopy-mri-guided-endovascular, 2 pgs.

Zhang et al., "Visual servoing control of soft robots based on finite element model," IEEE/RSJ International Conference on Intelligent Robots and Systems (IROS), 2017, 7 pgs.

Krebs et al. "Learning a Generative Motion Model from Image Sequences based on a Latent Motion Matrix." IEEE Transactions on Medical Imaging 40, No. 5, 2021, 12 pgs.

U.S. Appl. No. 17/249,651, filed Mar. 9, 2021 entitled "Multi-Task Learning Framework for fully Automated Assessment of Coronary Artery Disease," 39 pgs.

Jewell, "What Is Minimally Invasive Surgery?," 2018.

Lin et al., "Cycle Ynet: Semi-supervised Tracking of 3D Anatomical Landmarks." In International Workshop on Machine Learning in Medical Imaging, vol. 12436, 2020, pp. 593-602.

Zhang et al., "A Bottom-Up Approach for Real-Time Mitral Valve Annulus Modeling on 3D Echo Images," In International Conference on Medical Image Computing and Computer-Assisted Intervention, vol. 12266, Springer, Cham, 2020, pp. 458-467.

Mihalef et al., "Multi-scale models of the heart for patient-specific simulations," In Artificial Intelligence for Computational Modeling of the Heart, Academic Press, 2020, pp. 3-42.

Kim et al., "Evaluation of high-speed dynamic motions for robotic guidewire crossing techniques," In Proceedings of Hamlyn Symposium on Medical Robotics, London, United Kingdom. 2018, 2 pgs.

Miao et al., "Dilated fon for multi-agent 2d/3d medical image registration," In Proceedings of the AAAI Conference on Artificial Intelligence, 2018., vol. 32, No. 1, 8 pgs.

Extended European Search Report (EESR) mailed Mar. 28, 2023 in corresponding European Patent Application No. 22210396.2.

* cited by examiner

FIG 2

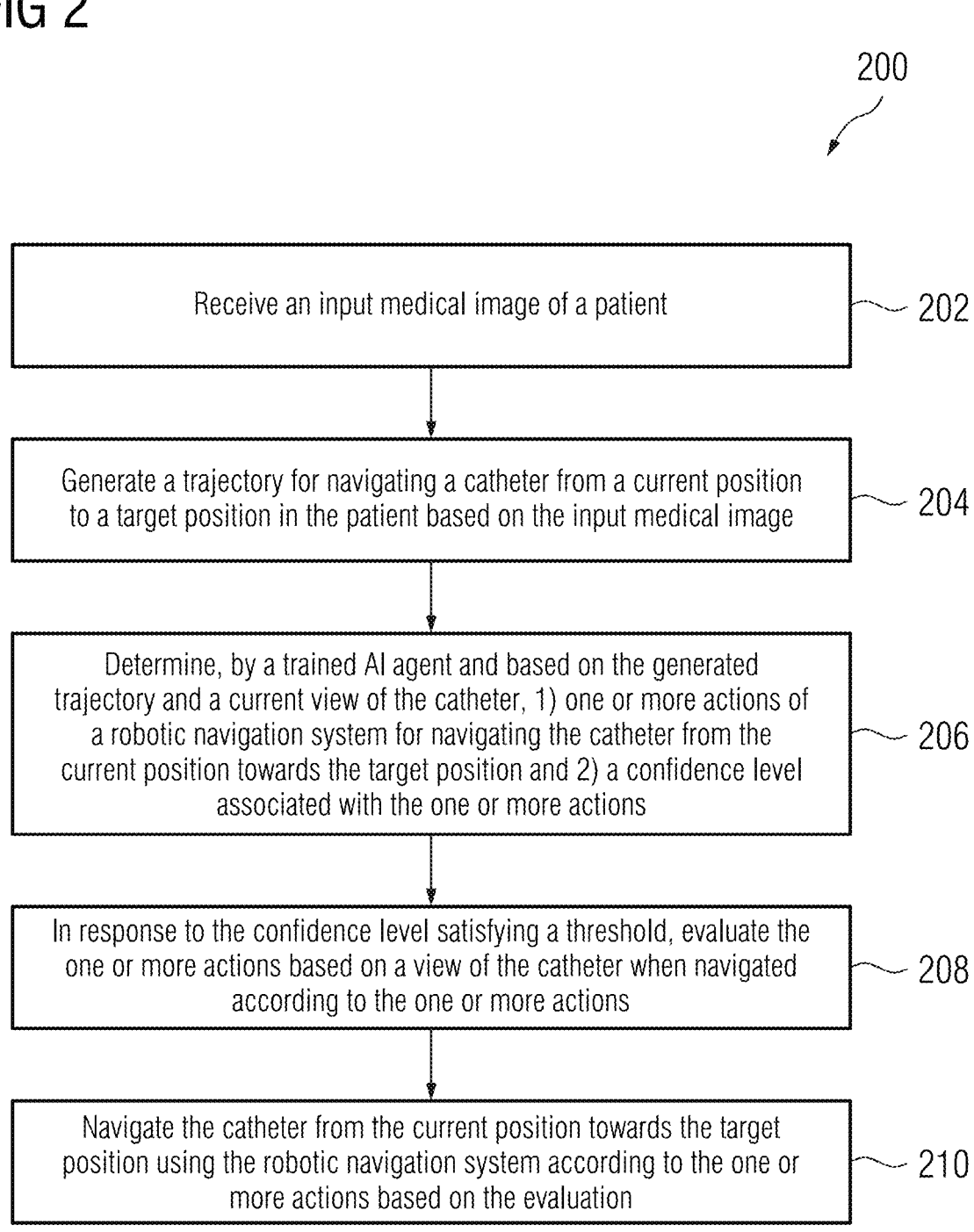

*200*

Receive an input medical image of a patient — 202

Generate a trajectory for navigating a catheter from a current position to a target position in the patient based on the input medical image — 204

Determine, by a trained AI agent and based on the generated trajectory and a current view of the catheter, 1) one or more actions of a robotic navigation system for navigating the catheter from the current position towards the target position and 2) a confidence level associated with the one or more actions — 206

In response to the confidence level satisfying a threshold, evaluate the one or more actions based on a view of the catheter when navigated according to the one or more actions — 208

Navigate the catheter from the current position towards the target position using the robotic navigation system according to the one or more actions based on the evaluation — 210

302

300

304

Angiography Image

Dense Block

Dense Block

Dense Block

Dense Block

Dense Block

Dense Block

Probability Heatmap

Dense Block 3 x 3 conv, BN, ReLU
2 x 2 max pooling
deconv with 80 filters
skip connection
1 x 1 conv, BN, ReLU

FIG 5
500
502
504
506
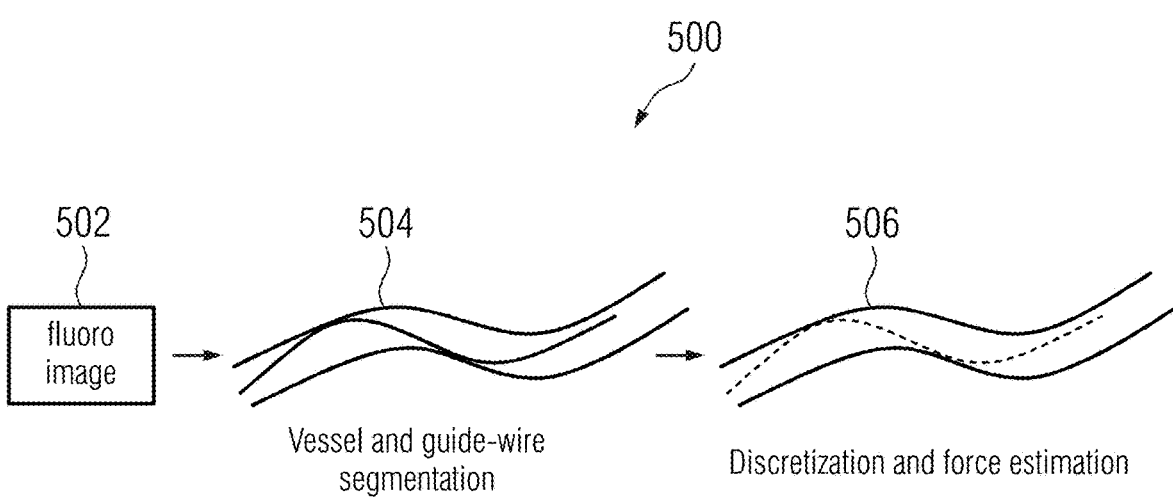
fluoro image
Vessel and guide-wire segmentation
Discretization and force estimation
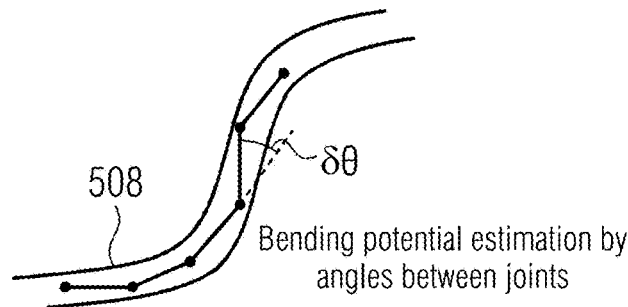
508
δθ
Bending potential estimation by angles between joints

Figure 6:
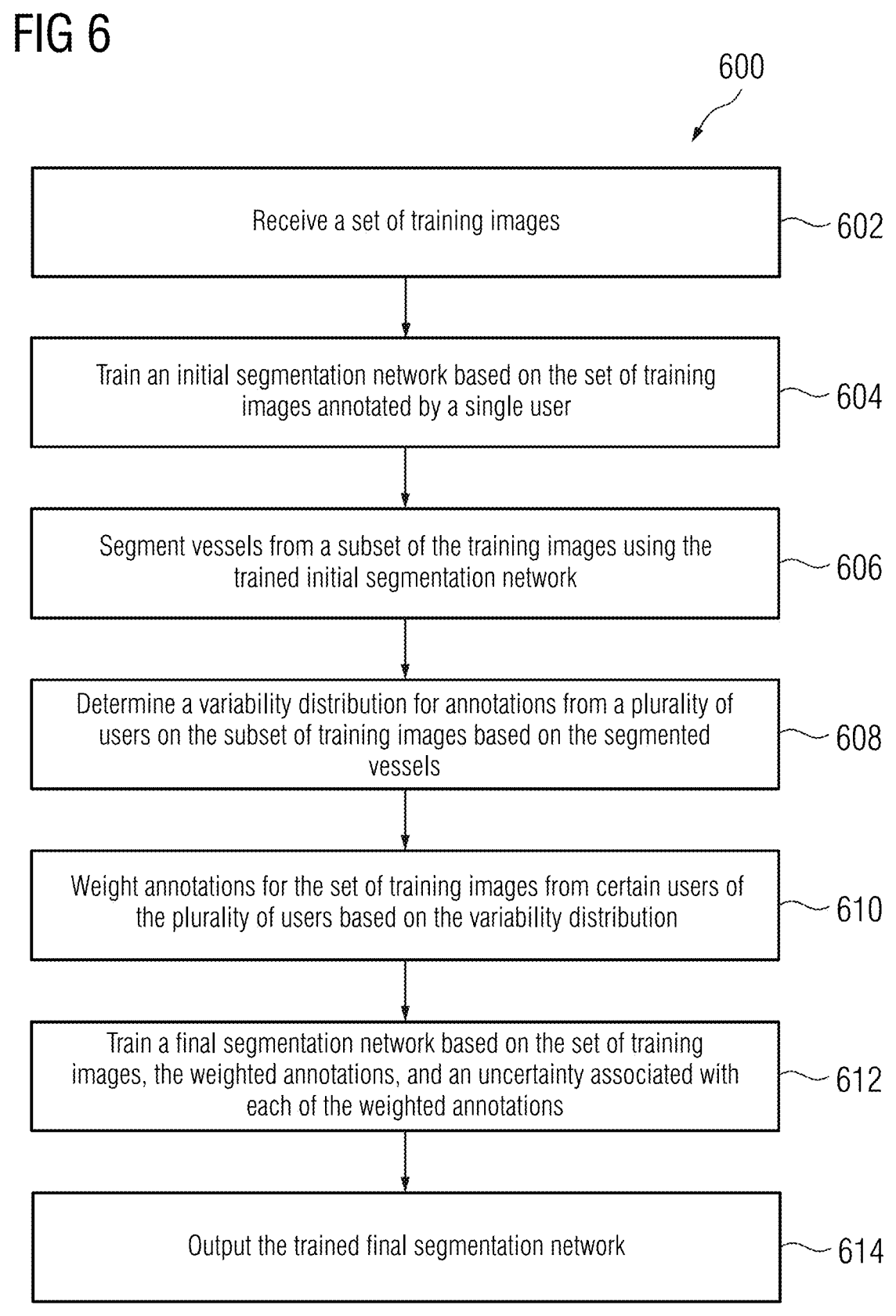

Receive a set of training images          ~602

Train an initial segmentation network based on the set of training images annotated by a single user          ~604

Segment vessels from a subset of the training images using the trained initial segmentation network          ~606

Determine a variability distribution for annotations from a plurality of users on the subset of training images based on the segmented vessels          ~608

Weight annotations for the set of training images from certain users of the plurality of users based on the variability distribution          ~610

Train a final segmentation network based on the set of training images, the weighted annotations, and an uncertainty associated with each of the weighted annotations          ~612

Output the trained final segmentation network          ~614

RISK MANAGEMENT FOR ROBOTIC CATHETER NAVIGATION SYSTEMS

TECHNICAL FIELD

The present invention relates generally to robotic catheter navigation, and in particular to risk management for robotic catheter navigation systems.

BACKGROUND

Robotic catheter navigation systems have been developed to assist surgeons in performing minimally invasive surgery. Such robotic catheter navigation systems ease the difficulty in surgeon training and reduce the exposure of surgeons to radiation. However, despite the advantages, robotic catheter navigation systems have not been widely adopted. This is due to the risk and uncertainty associated with robotic catheter navigation systems.

BRIEF SUMMARY OF THE INVENTION

In accordance with one or more embodiments, systems and methods for risk management in robotic catheter navigation systems are provided. An input medical image of a patient is received. A trajectory for navigating a catheter from a current position to a target position in the patient is determined based on the input medical image using a trained segmentation network. One or more actions of a robotic navigation system for navigating the catheter from the current position towards the target position and a confidence level associated with the one or more actions are determined by a trained AI (artificial intelligence) agent and based on the generated trajectory and a current view of the catheter. In response to the confidence level satisfying a threshold, the one or more actions are evaluated based on a view of the catheter when navigated according to the one or more actions. The catheter is navigated from the current position towards the target position using the robotic navigation system according to the one or more actions based on the evaluation.

In one embodiment, the trajectory is generated by generating a colored dynamic roadmap of vessels in the input medical image comprising color coding to indicate uncertainty. The uncertainty is quantified by a trained segmentation network. To train the trained segmentation network, a set of training images is received. An initial segmentation network is trained based on the set of training images annotated by a single user. Vessels are segmented from a subset of the set of training images using the trained initial segmentation network. A variability distribution for annotations from a plurality of users for the subset of training images is determined based on the segmented vessels. Annotations for the set of training images from certain users of the plurality of users are weighted based on the variability distribution. A final segmentation network is trained based on the set of training images, the weighted annotations, and an uncertainty associated with each of the weighted annotations. The trained final segmentation network is output.

In one embodiment, in response to the confidence level not satisfying the threshold, the AI agent is moved to a previous position in the trajectory. The trajectory is optimized for navigating the catheter from the previous position to the target position. The AI agent is placed at a position in the optimal trajectory closest to the current position. Navigation of the catheter by the AI agent is restarted using a view of the catheter at the position in the optimal trajectory closest to the current position as the current view. The trajectory is optimized based on possible actions of the robotic navigation system and a segmentation of vessels in from the input medical image.

In one embodiment, the one or more actions are evaluated by determining whether the view of the catheter when navigated according to the one or more actions is out-of-domain of training data on which the trained AI agent is trained. In another embodiment, the one or more actions are evaluated by evaluating a bending stress and a number of punctures of a guidewire for navigating the catheter.

In one embodiment, a configuration of the robotic navigation system while a user performs a set of actions navigating the catheter is stored. The set of actions is replayed based on the stored configuration of the robotic navigation system.

In one embodiment, user input selecting a position at which the catheter is to navigate is received. Kinematics for navigating the catheter to the selected position are computed. The catheter is navigated to the selected position based on the computed kinematics.

In one embodiment, a safety margin is computed for a path in the input medical image. Haptic feedback is provided to a user navigating the catheter based on a current position of the catheter with respect to the safety margin.

These and other advantages of the invention will be apparent to those of ordinary skill in the art by reference to the following detailed description and the accompanying drawings.

BRIEF DESCRIPTION OF THE DRAWINGS

FIG. 2 shows a method for automatic catheter navigation with risk management, in accordance with one or more embodiments;

FIG. 5 shows a workflow for catheter status evaluation, in accordance with one or more embodiments;

FIG. 6 shows a method for training a segmentation network for segmenting vessels and quantifying a level of uncertainty associated with the segmentation, in accordance with one or more embodiments;

FIG. 9 shows a convolutional neural network that may be used to implement one or more embodiments.

DETAILED DESCRIPTION

The present invention generally relates to methods and systems for risk management for robotic catheter navigation systems. Embodiments of the present invention are described herein to give a visual understanding of such methods and systems. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Conventional robotic catheter navigation systems are typically implemented using pretrained machine learning models. Catheter navigation using conventional robotic catheter navigation systems are associated with a number of risks factors. For example, one risk factor is out-of-domain input data, where the input data of the machine learning model is out-of-domain of the training data on which the machine learning model is trained. Another risk factor is model limitation, wherein the machine learning model is limited due to uncertainty in the annotation of training data or due to limited training data. A further risk factor is risk associated with the catheter/guidewire, where pressure or punctures of the vessel boundary by the catheter/guidewire may result in hemorrhage or hematoma.

Embodiments described herein provide for managing the risk associated with robotic catheter navigation systems. In one embodiment, a colored dynamic roadmap is provided to expose risk and uncertainty to users during catheter navigation with a color-coded roadmap. In another embodiment, low-confidence movement risks, OOD (out-of-domain) risks, and catheter status risks are quantified and remedy solutions are provided. Advantageously, embodiments described herein help to prevent high risk movements when navigating a catheter.

Figure 1:
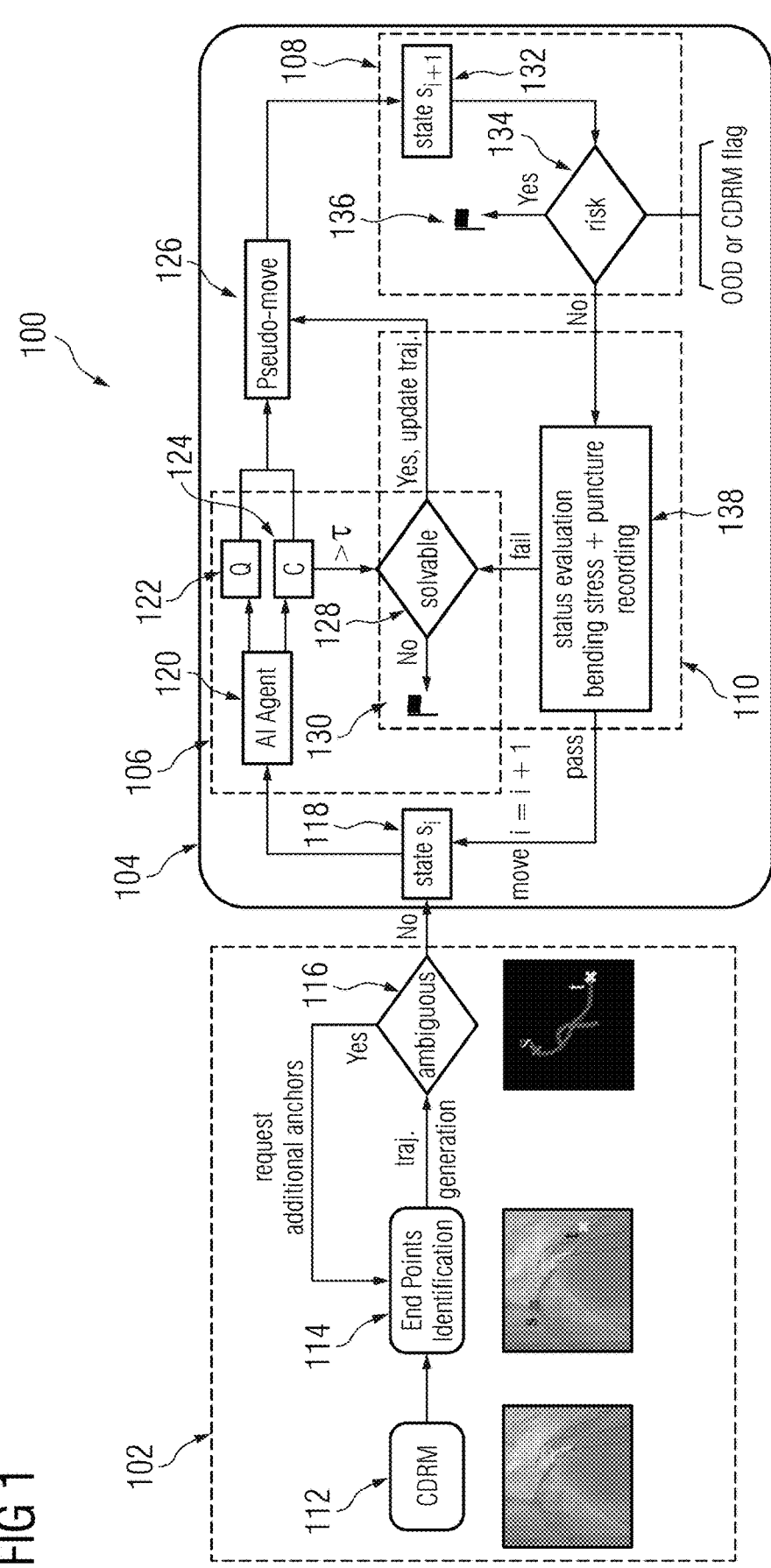
FIG. 1 shows a workflow for automatic catheter navigation with risk management, in accordance with one or more embodiments.

FIG. 1 shows a workflow 100 for automatic catheter navigation with risk management, in accordance with one or more embodiments. Workflow 100 comprises two stages: a trajectory generation stage 102 for generating a trajectory for navigating the catheter from a current position to a target position and an agent navigation stage 104 for navigating the catheter from the current position towards the target position based on the generated trajectory. FIG. 1 will be continually referred to with regards to FIGS. 2-6.

FIG. 2 shows a method 200 for automatic catheter navigation with risk management, in accordance with one or more embodiments. The steps of method 200 may be performed by one or more suitable computing devices, such as, e.g., computer 1002 of FIG. 10.

At step 202 of FIG. 2, an input medical image of a patient is received. The input medical image may depict vessels (e.g., coronary arteries) of the patient in which a catheter is to be navigated. The input medical image may be of any suitable modality, such as, e.g., MRI (magnetic resonance imaging), CT (computed tomography), US (ultrasound), x-ray, and/or any other medical imaging modality or combinations of medical imaging modalities. The input medical image may be a 2D (two dimensional) image or 3D (three dimensional) volume, and may comprise a single image or a plurality of images (e.g., to form a 2.5D image). The input medical image may be received directly from an image acquisition device, such as, e.g., a CT scanner, as the image is acquired, or can be received by loading a previously acquired image from a storage or memory of a computer system (e.g., a PACS (picture archiving and communication system)) or by receiving an image that have been transmitted from a remote computer system.

At step 204 of FIG. 2, a trajectory for navigating a catheter from a current position to a target position in the patient is generated based on the input medical image. In one example, as shown in FIG. 1, the trajectory may be generated during trajectory generation stage 102 of workflow 100.

Figure 3:
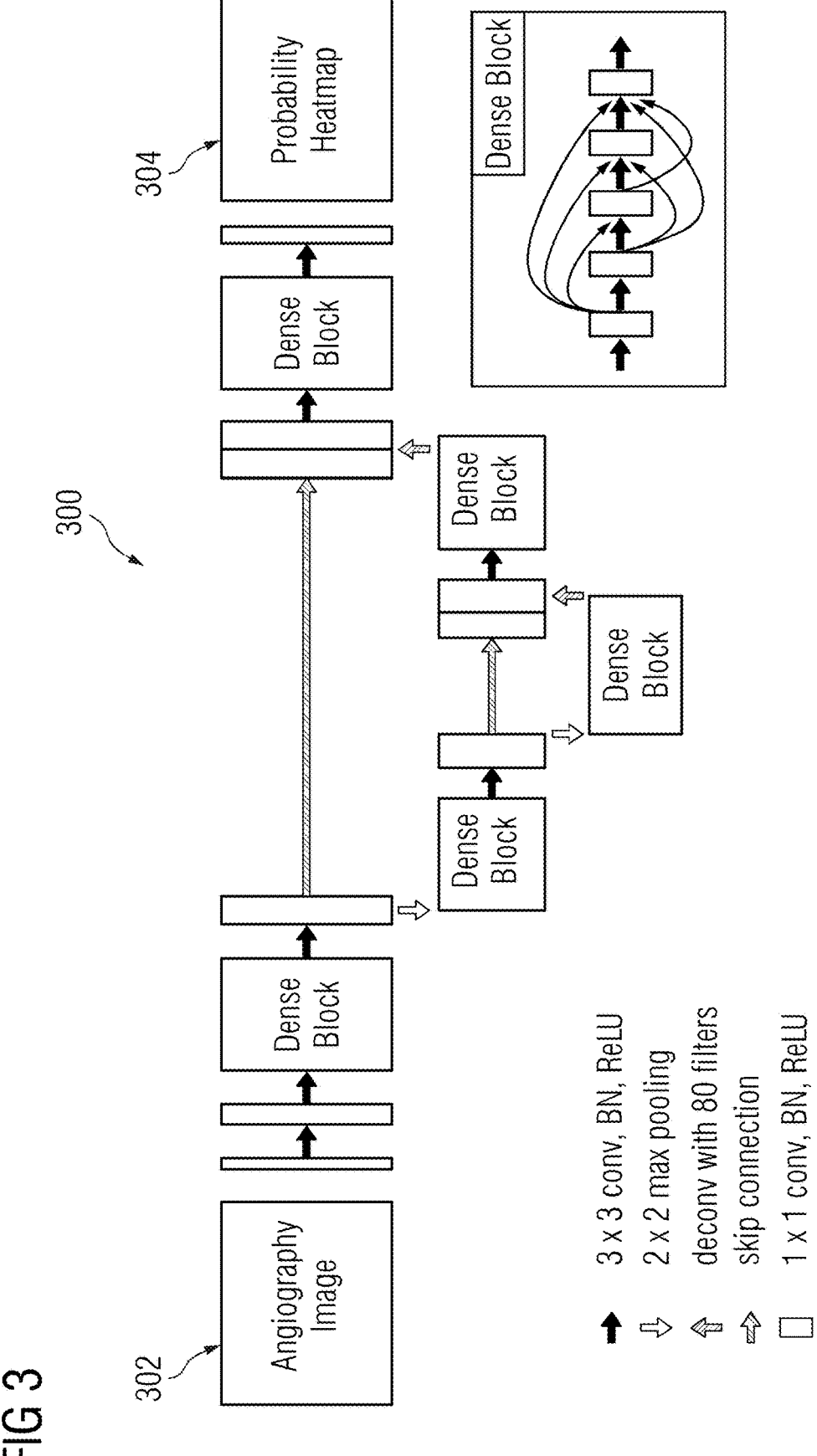
FIG. 3 shows an exemplary network architecture of a segmentation network, in accordance with one or more embodiments.

During trajectory generation stage 102, a CDRM (colored dynamic roadmap) 112 is first generated from the input medical image. CDRM 112 is a roadmap of the vessels of the patient with color coding to indicate a level of uncertainty. The uncertainty may be due to data annotation uncertainty and model prediction uncertainty. CDRM 112 is generated by segmenting the vessels from the input medical image using a trained machine learning based segmentation network. The segmentation network receives as input the input medical image and generates as output a corresponding probability map representing a pixel-wise segmentation of the vessels with the level of uncertainty encoded therein. An exemplary machine learning based segmentation network is shown in FIG. 3. Training the segmentation network to segment vessels from the input medical image and quantifying the level of uncertainty associated with the segmentation is further described below with respect to FIG. 6.

FIG. 3 shows an exemplary network architecture of a segmentation network 300, in accordance with one or more embodiments. Segmentation network 300 is implemented in FIG. 3 as a denseUNet. Segmentation 300 receives as input an angiography image 302 and generates as output a probability heatmap 304. Probability heatmap 304 has the same size as angiography image 302. Each pixel of probability heatmap 304 has a value between 0 and 1, representing a level of uncertainty associated with the vessel segmentation such that a 0 indicates that no vessel is shown on the corresponding pixel and a 1 indicates 100% certainty (i.e., no uncertainty) that a vessel is shown on the corresponding pixel. Accordingly, probably heatmap 304 represents the segmentation of the vessels from angiography image 302 with the level of uncertainty encoded therein. While segmentation network 300 is shown in FIG. 3 as being implemented as a denseUNet, it should be understood that segmentation network 300 may be implemented according to any suitable machine learning based network, such as, e.g., a UNet, fully convolutional networks, etc.

Returning back to trajectory generation stage 102 of FIG. 1, the trajectory for navigating the catheter from the current position to the target position is determined from CDRM 112. To generate the trajectory, end point identification 114 is performed in CDRM 112 by identifying a current position and a target position. For example, user input may be received identifying the current position and the target position in CDRM 112. Vessel paths between the current position and the target position are extracted from CDRM 112 as the trajectory. If the trajectory is determined to be ambiguous, at decision block 116, additional anchor points are requested (e.g., from the user). The additional anchor points comprise one or more points that will be between the current position and the target position in the trajectory. The trajectory is extracted from CDRM 112 based on the additional anchor points, along with the current position and the target position. If the trajectory is determined not to be ambiguous, at decision block 116, the trajectory is output to an AI (artificial intelligence) agent in agent navigation stage 104 to navigate the catheter from the current position to the target position.

In one embodiment, the trajectory is ambiguous where the pathway, which is along the vessel between the current position and target position is not continuous. This could be due to a segmentation error from CDRM 112 or due to a wrong point set by the user. In this scenario, user input is received from the user manual delineating the non-continuous part or corrects the input to define a pathway from the current position to the target position. In another embodiment, the trajectory is ambiguous where there are multiple pathways that connect the current position to the target position. Since in the real world, the vessel is a 3D structure and the segmented CDRM 112 is its 2D projection, there may be self-crossing of the vessels (shown in FIG. 1 at decision block 116). From the image perspective, there are multiple pathways that can lead from the current position to the target position. However, given the tree structure of the 3D vessel, in the real world, there usually only exists one path. In this scenario, user input is received from the user manually highlighting the correct pathway and remove the incorrect pathways.

At step 206 of FIG. 2, it is determined, by a trained AI agent and based on the generated trajectory and a current view of the catheter, 1) one or more actions or a robotic navigation system for navigating the catheter from the current position towards the target position and 2) a confidence level associated with the one or more actions. In one example, as shown in FIG. 1, AI agent 120 is trained to observe a current state $s_i$ 118 to predict Q-values 122 and an uncertainty C 124 associated with each possible action of the robotic navigation system for navigating the catheter. Current state $s_i$ 118 is an image of the current view of the catheter. Q-values 122 represent an expected reward for taking the associated action. In one example, the possible actions of the robotic navigation system for navigating the catheter comprise rotate on retract (ROR, automatically rotate the guidewire upon retraction), wiggle (automatically oscillate the guidewire during advancement), spin (rotation of guidewire), dotter (back and forth motion as the catheter advances), and constant speed. The possible actions of the robotic navigation system are constrained by the generated trajectory. AI agent 120 cannot perform an action that moves it away from the generated trajectory. AI agent 120 selects the action (from the constrained set of actions) with the highest Q-value 122. AI agent 120 may be implemented accordance to known techniques.

At step 208 of FIG. 2, in response to the confidence level satisfying a threshold, the one or more actions are evaluated based on a view of the catheter when navigated according to the one or more actions.

As shown in FIG. 1, the confidence level is evaluated by low-confidence movement assessment component 106. Low-confidence movement assessment component 106 addresses uncertainty due to a determined action having high uncertainty. Low-confidence movement assessment component 106 will be described with reference to FIG. 4, showing a workflow 400 for low-confidence movement assessment, in accordance with one or more embodiments.

Figure 4:
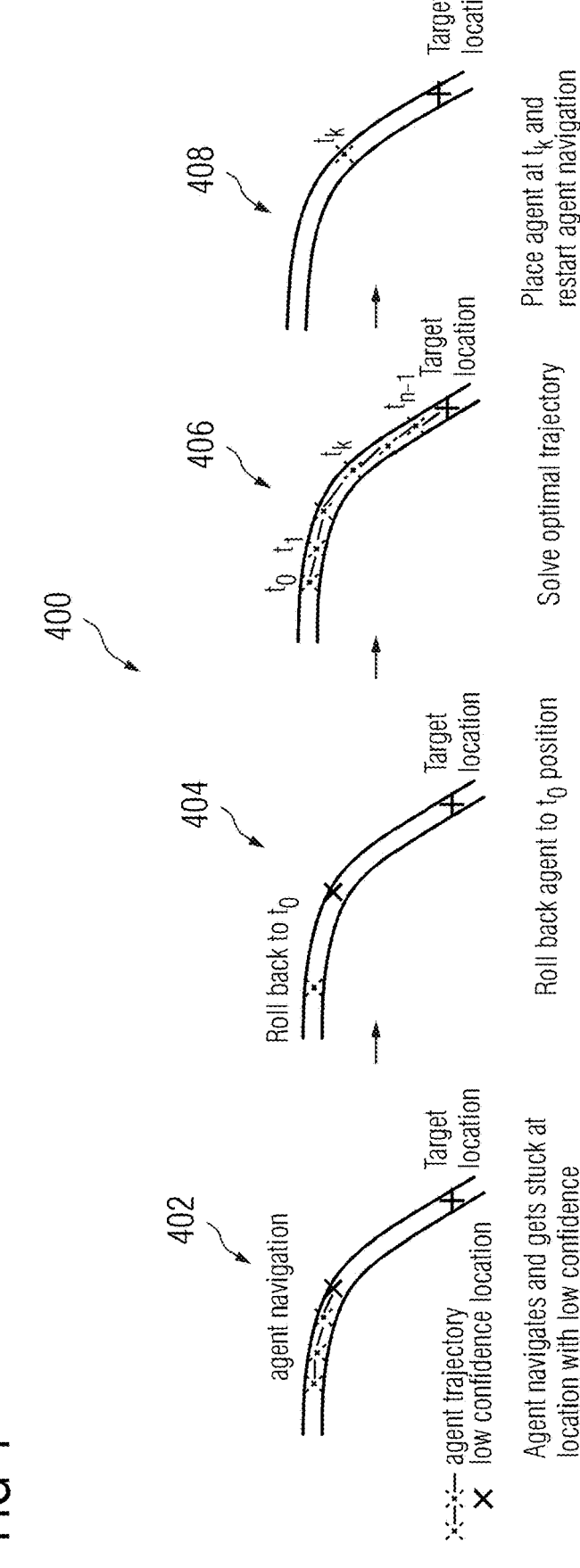
FIG. 4 shows a workflow for low-confidence movement assessment, in accordance with one or more embodiments.

At step 402 of FIG. 4, the AI agent navigates and gets stuck at a location with low confidence. The uncertainty C 124 is compared with a predetermined threshold τ to determine if AI agent 120 is located at a position with low confidence. If uncertainty C 124 satisfies threshold (e.g., C>τ, meaning not low confidence), workflow 100 proceeds to pseudo-move 126 where the one or more actions are evaluated based on a view of the catheter when navigated according to the one or more actions (i.e., based on a next state $s_{i+1}$). If uncertainty C 124 does not satisfy threshold τ (e.g., C<τ, meaning low confidence), AI agent moves back to a prior state at a previous position in the trajectory and determines an optimized trajectory from the previous position to the target position. In one example, as shown in FIG. 4, at step 404, the AI agent rolls tack to a previous location $t_0$ and, at step 406, an optimal trajectory is solved.

The optimal trajectory is determined using a trajectory optimization algorithm. Given an initial trajectory $T_0 = t_0$, $t_1, \ldots t_N$, each step $t_i$ is represented as a tuple of two values $(x_i, y_i)$ indicating the x,y coordinate of the catheter tip in the image. The objective function for determining the optimal trajectory is given as follows:

$$f(T) = \sum_{i=1}^{N-1} \|t_{i+1} - t_i\|^2 + s(T) \qquad \text{(Equation 1)}$$

where s(T) represents the total bending potential of trajectory T over the vessel. Trajectory optimization can be described as a non-convex problem as follows:

$$\min_T f(T)$$

subject to the following constraints:

$$t_{i+1} = g_w(t_i), \quad i = 0, \ldots, N-1$$

$$t_i \in V, \quad i = 0, \ldots, N-1$$

where function $g_w$ represents the action space of all possible actions of the robotic navigation system and V represents the segmented vessel from the input medical image.

In the first constraint, $t_{i+1} = g_w(t_i)$, the trajectory is constrained to the possible actions of the robotic navigation system because of the material nature of the guidewire of the catheter. The guidewire cannot perform arbitrary movement in space but instead, given a current position to, the choice of the next position $t_1$ can only have limited possibilities. Mathematically, this constraint is equivalent to the following:

$$t_{i+1} = w_1 ror(t_i) + w_2 \text{wiggle}(t_i) + w_3 \text{spin}(t_i) + w_4 \text{dotter}(t_i)$$

where $\|w\|_0 = 1$ and $w_1$, $w_2$, $w_3$, $w_4$ are weights.

In the second constraint, $t_i \in V$, each step of the trajectory is constrained to be in the segmented vessel V given by CDRM 112. This constraint ensures the trajectory must be within the vessel.

This optimization problem is non-convex (i.e., more than one optimal solution exists) and difficult to solve due to the exponential search space growth from the constraint $t_{i+1} = g_w(t_i)$. This constraint is therefore relaxed with $l_1$ relaxation, i.e., $\|w\|_1 \leq 1$. The optimization problem then becomes (with a Lagrangian):

$$\min_{T,w} f(T) + \lambda \sum_{i=0}^{N-1} \left( \sum_{j=1}^{4} w_i^j(t_i) - t_{i+1} \right)^2$$

subject to the following constraints:

$$\|w^j\|_1 \leq 1, \quad i = 0, \ldots, N-1$$

$$t_i \in V, i = 0, \ldots, N-1.$$

Solving the above optimization problem can give the optimal trajectory T. If an optimal trajectory T is solvable, at determination block 128, the trajectory is updated with the optimal trajectory and workflow 100 proceeds to pseudo-move 126. The AI agent is positioned at a position in the optimal trajectory nearest to the current position but closer to the target position and the AI agent continues navigation using its own network. For example, at step 408 of FIG. 4, the AI agent is placed at position $t_k$ and navigation is restarted. Accordingly, method 200 returns to step 206 using the view of the catheter at position $t_k$ as the current view. Otherwise, if an optimal trajectory T is not solvable, at determined block 128, a flag 130 is raised requesting user input. The user input may include, for example, manual navigation of the catheter or robot repositioning.

Determining the optimal trajectory is not immediately performed as the trajectory optimization is independent of image features. As is seen in the optimization problem, only the vessel tree position feature V is included in the optimization and no image features or vessel appearance features are used. The AI agent, on the other hand, leverages the visual features and can make action decisions adaptively. For example, some of the steps $t_i$ produced by the trajectory optimization may be too close to the boundary of the vessel where operating the robot can give a high risk. The AI agent may find a better trajectory that keeps the operating risk low.

At pseudo-move 126, the one or more actions are evaluated based on a view of the catheter when navigated according to the one or more actions (i.e., based on a next state. At OOD detection component 108, next state $s_{i+1}$ 132, representing an image of a view of a catheter when navigated according to the one or more actions, is evaluated to determine whether next state $s_{i+1}$ 132 is out-of-domain of the training data on which AI agent 120 is trained. In other words, OOD detection determines whether AI agent 120 has seen this image before during the training. OOD detection component 108 prevents AI agent 120 from making random movements.

In one embodiment, to provide OOD estimation on next state $s_{i+1}$ 132, patches are (e.g., randomly) extracted from the training data on which AI agent 120 is trained. Binary labeling is performed on each respective patch using the following rules. Firstly, if there is no vessel depicted in the respective patch, label the respective patch as 0. Secondly, if vessels are depicted in the respective patch, AI agent 120 is applied to the respective patch. If AI agent 120 is able to perform correct navigation (i.e., the movement is legit), label the respective patch as 1 and otherwise 0. A binary classifier is then trained to classify images as being OOD using the labeled patches.

If next state $s_{i+1}$ 132 is determined to be OOD and therefore a risk, at decision block 134, a flag 136 is raised requesting user input. The user input may include, for example, manual navigation of the catheter until a state is reached that is not OOD (i.e., in distribution of the training data on which AI agent 120 is trained). If next state $s_{i+1}$ 132 is determined to not be OOD, at decision block 134, workflow 100 proceeds to catheter status evaluation component 110.

At catheter status evaluation component 110, the overall status of the catheter is evaluated, including the bending stress and the total number of punctures of the guidewire onto the vessel wall since the beginning of navigation. High pressure or frequent punctures could cause severe hemorrhage or hematoma. Such damage to the patient may not be directly visualized from fluoroscopy images. Catheter status evaluation component 110 will be described with reference to FIG. 5, showing a workflow 500 for catheter status evaluation, in accordance with one or more embodiments.

Status evaluation 138 evaluates the bending stress of the catheter by first segmenting the vessel and the guidewire to extract the relative location of the guidewire with respect to the vessel. For example, as shown in FIG. 5, vessel and guidewire segmentation is performed from fluoroscopic image 502 at step 504. The elastic potential of the guidewire is then estimated. Given the segmented guidewire (i.e., a line), the guidewire is discretized into segments. The elastic potential of the guidewire is estimated based on the angles between the segments as follows:

$$e = \sum_{i}^{n} \frac{EI}{2L} \times \delta\theta_i^2 \qquad \text{(Equation 2)}$$

where E is the Young's modulus of the guidewire, I is the moment of inertia, and $\delta\theta$ is the angle between two consecutive segments. For example, as shown in FIG. 5, discretization and force estimation is performed at step 506. The bending stress between two segments is proportionate to the angles between the two segments, i.e., $\sigma = k|\delta\theta|$. Given a trajectory of the catheter $T_0 = t_0, t_1, \ldots t_N$, by defining $\delta\theta_i$ as the angles between $t_{i-1} - t_i$ and $t_i - t_{i+1}$, the elastic potential of the trajectory s(T) can be calculated according to Equation 2. For example, the bending potential estimation is determined based on angles between joints at step 508.

The total number of punctures of the guidewire onto the vessel wall may be determined using any suitable approach. In one embodiment, the total number of punctures can be determined by manually inspecting the vessel walls by the user (e.g., from X-ray imaging), by automatically counting how many times the robot gives the vessel boundary a hard push (the definition of what is 'hard' is determined by the user), or by adding a small pressure sensor to the tip of the guidewire and counting the times when the pressure is above a user-defined threshold.

Status evaluation 138 fails where the bending stress of the guidewire or the number of punctures does not satisfy a predetermined threshold. If status evaluation 138 fails, workflow 100 returns to decision block 128 to determine if an optimal trajectory is solvable. If not, flag 130 is raised. For example, flag 130 may be an over-stress alert to a user. If status evaluation 138 passes, the catheter is navigated according to the determined one or more actions.

At step 210 of FIG. 2, the catheter is navigated from the current position towards the target position using the robotic navigation system according to the one or more actions based on the evaluation. Method 200 may return to step 206 to repeat steps 206-210 for any number of iterations using the view of the catheter as navigated according to the one or more actions as the current view to iteratively navigate the catheter to the target position.

FIG. 6 shows a method 600 for training a segmentation network for segmenting vessels and quantifying a level of uncertainty associated with the segmentation, in accordance with one or more embodiments. The steps of method 600 may be performed by one or more suitable computing devices, such as, e.g., computer 1002 of FIG. 10. The steps of method 600 are performed to train a segmentation network during a prior offline or training stage. Once trained, the trained segmentation network is applied during an online or testing stage to segment vessels from input medical images and quantifying a level of uncertainty associated with the segmentation. In one example, method 600 may be performed to train the segmentation network utilized at step 204 of FIG. 2 for generating a CDRM.

At step 602 of FIG. 6, a set of training images is received. The set of training images is denoted $x_i$, where i=1, ..., n. The training images depict vessels of patients. The training images may be of any suitable modality, such as, e.g., MRI, CT, US, x-ray, and/or any other medical imaging modality or combinations of medical imaging modalities. The training images may be a 2D image or 3D volume, and may comprise a single image or a plurality of images (e.g., to form a 2.5D image). The training images may be received directly from an image acquisition device, such as, e.g., a CT scanner, as the images are acquired, or can be received by loading previously acquired images from a storage or memory of a computer system (e.g., a PACS) or by receiving images that have been transmitted from a remote computer system.

At step 604 of FIG. 6, an initial segmentation network $M_0$ is trained based on the set of training images annotated by a single user. The initial segmentation network $M_0$ may be implemented according to the network architecture 300 of FIG. 3.

At step 606 of FIG. 6, vessels are segmented from a subset of the training images using the trained initial segmentation network $M_0$.

At step 608 of FIG. 6, a variability distribution for annotations from a plurality of users on the subset of training images is determined based on the segmented vessels. The subset of training images may be (e.g., randomly) sampled subset of the set of training images. The variability distribution defines, for each pixel to be annotated, how many users annotate it (e.g., as background). In other words, the variability distribution is a binary distribution for each pixel counting the number of users that annotate the pixel as a vessel versus as background. It should be very consistent for pixels that are far from the vessel or parts of the vessel that are very clear, but variability comes for the pixels that are less clear such as pixels on minor vessel branches or vessel boundaries. The variability distribution may be determined by evaluating an accuracy of the trained initial segmentation network by comparing the segmented vessels determined using the trained initial segmentation network with the annotations form the plurality of users. K-means clustering is then performed on the accuracy.

At step 610 of FIG. 6, annotations for the set of training images from certain users of the plurality of users is weighted based on the variability distribution. The certain users may be (e.g., arbitrarily) selected from the plurality of users. The weighted annotations are denoted $$\sum_{i=1}^{k} w_i y^i,$$

where $w_i$ represents the weight associated with certain user i and $y^i$ represents the binary mask annotated by certain user i. The weights $w_i$ are meant to aggregate annotations from all users while promoting annotations from more experienced annotators. The weights $w_i$ may be user defined such that larger weight may are assigned to more experienced users. All weights $w_i$ are be non-negative.

At step 612 of FIG. 6, a final segmentation network $M_f$ is trained based on the set of training images, the weighted annotations, and an uncertainty associated with each of the weighted annotations. The uncertainty associated with each of the weighted annotations is calculated as:

$$y = \exp\left(-\frac{\|x - x_c\|^2}{\sigma^2}\right)$$

(Equation 3)

where $x_c$ represents the centerline of the annotated vessel segmentation. In accordance with Equation 3, the uncertainty of the annotated vessel segmentation is defined to increase from the centerline of the vessels to the boundary of the vessels.

At step 614 of FIG. 6, the trained final segmentation network is output. For example, the trained final segmentation network can be output by storing the trained final segmentation network on a memory or storage of a computer system, or by transmitting the trained final segmentation network to a remote computer system. The trained final segmentation network may be applied during an online or inference stage (e.g., at step 204 of FIG. 2) for generating the CDRM.

At times, a user may manually navigate the catheter via the robotic navigation system. Various embodiments are provided as follows to facilitate user navigation of the catheter.

In one embodiment, trajectory-based navigation is provided. In trajectory-based navigation, robot trajectories, comprising a set of actions performed by a user during a procedure at an initial time, may be replayed at any future time during the procedure. The robot trajectories are compositions of simple (e.g., translation, rotation, etc.) and/or complex (e.g., fast rotate-and-push, rotate-and-retract, etc.) actions performed by the user during the procedure. To record the robot trajectories, the configuration of the robotic navigation system while the user performs the set of actions is stored (e.g., in memory or storage). The saved configuration of the robotic navigation system may then be retrieved at a future point in time to replay the robot trajectories. The robot trajectories may be replayed using trajectory-bounded control such that the actions of the trajectories are reproduced in a forward or backward direction, with accelerated or decelerated speed, etc. Trajectory-based navigation enables the repetition of very precise manipulations with a simple and unambiguous unidimensional user interface, which could be implemented using motion sensing, foot pedals, voice control, etc. Advantageously, robot trajectories may be stored at the beginning of the procedure for a specific catheter and replayed for other catheters in over-the-wire setups, for example. Additionally, stored trajectories could be used to enable non-expert operators to operate the robot to handle potential complications, for example, in a multi-operator setup in remote settings. In the case of the robot manipulating an imaging catheter, the trajectories could be replayed to visualize the same location several times over the procedure with high precision for, e.g., therapy delivery or complication monitoring.

In one embodiment, "follow-me" navigation is provided. In this embodiment, the user does not manipulate the catheter directly but rather selects points on a user interface a relatively short distance from the current position of the catheter. The user thereby progressively pulls the catheter to the target position. For every selection, the path from the current position of the tip of the catheter to the selected point is computed on the overall path planned at the beginning of the procedure. Inverse kinematics are computed from tip position to robot joint space and computed torques are applied to the robot to navigate the tip of the catheter to the selected position. This process may be repeated until the user stops selected points or until a target position is reached. Advantageously, "follow-me" navigation provides for an intuitive way of controlling the catheter, since the user can focus on where the catheter should be navigated instead of how to manipulate the catheter. The learning curve is therefore significantly lower. Robot control can also be performed on a mobile device, allowing arrangement of the operating room in a more efficient manner. Advanced safety mechanisms can also be implemented by, for example, watch-dog rules to prevent the catheter from perforating a vessel, going in the wrong direction, etc.

In one embodiment, vision-based haptic feedback is provided based on real-time imaging, prior information from preoperative images (e.g., CT/MR images), computational modeling of vessels and vessel/catheter interaction, and robotic state sensors. Vision-based haptic feedback enables feedback felt by a user manipulating a joystick when a catheter navigates outside a safety margin (e.g., towards vessel walls). To implement vision-based haptic feedback, path planning in the vessel tree is computed from either preoperative images or multiple angio-views. If using preoperative images, 3D/2D deformable registration is performed to fuse the path plan to the patient anatomy. If using multiple angio-views, vessels are segmented from the angiograms, point matching between segmentations in the multiple views is performed, and 3D vessel lumen and centerlines are reconstructed from the multiple views. A safety margin is then computed from the path planning and vessel lumen. The safety margin may consider, for example, uncertainty in lumen segmentation and catheter tracking, vessel health/presence of plaque, known stiffness of the catheter, etc. The catheter tip is automatically tracked during robotic manipulation. When the catheter tip is within the safety margin, visual feedback and/or haptic feedback may be provided. The haptic feedback may be a force on the joystick, which is navigating the catheter, that is proportional to the distance of the catheter tip within the safety margin. Alternatively, the feedback may be a force on the joystick correlated to an equivalent force applied by the vessel wall to the catheter, estimated using imaging and real-time computational modeling of vessel-catheter interaction. The preoperative images are reregistered to the live images to keep accuracy whenever needed (e.g., triggered by an accuracy watchdog module). With this system, the user receives haptic feedback, which could potentially be more complete than what the user conventionally feels when manipulating the catheter since the haptic feedback would be directly correlated with the position of the catheter tip. Furthermore, the feedback could be transmitted in various ways: visually, resistive force in the joystick or other user interface, vibration of a mobile device or wearable devices, etc.

Figure 7A:
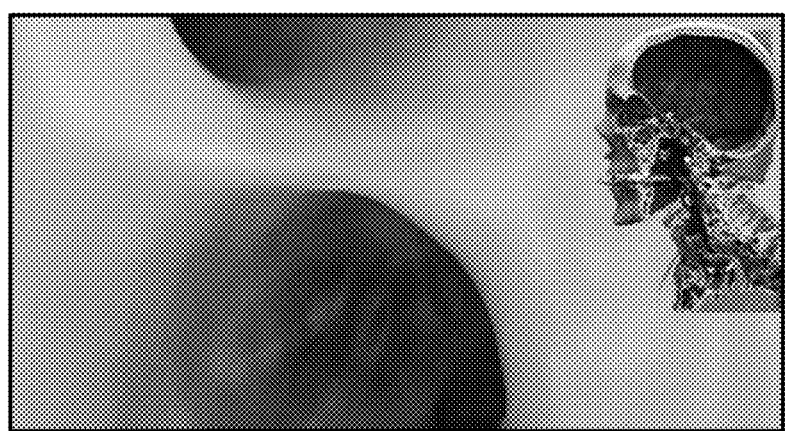
FIG. 7A shows an image of a "first-person" rendering, in accordance with one or more embodiments.
Figure 7B:
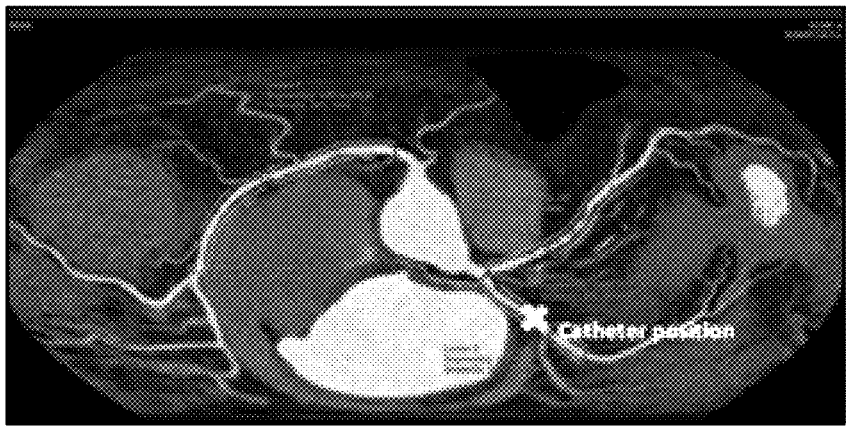
FIG. 7B shows an image of a Mercator rendering, in accordance with one or more embodiments.

In one embodiment, a visualization of vessels is provided. This embodiment provides for visualizing catheter motion during the procedure by a "first-person" rendering or a Mercator rendering. The "first-person" rendering is a visualization of the view of the catheter. The Mercator rendering is a flattened visualization of the vessels from 3D preoperative images. To generate the visualizations (either the "first-person" or the Mercator), preoperative images are co-registered to the real-time angiography images. The following are performed in real-time (i.e., at the same frame-rate as the fluoroscopy images): 1) real-time tracking of the catheter tip in fluoroscopy images is performed, combined with robotic information; 2) mapping catheter position to the preoperative images; 3) generating "first-person" rendering views of the vessel; 4) projecting the catheter tip position on the Mercator map of vessels and visualize the catheter on the map; and 5) in both the "first person" rendering and the Mercator map, color code the tissue types for easier navigation based on, e.g., the image segmentation. The preoperative images are re-registered to the live angiography images to maintain accuracy when needed. FIG. 7A shows an image 700 of a "first-person" rendering and FIG. 7B shows an image 710 of a Mercator rendering, in accordance with one or more embodiments. The visualizations provided herein allow for more precise analysis of the tissue environment around the catheter while enabling more intuitive way to navigate by removing the mental projection necessary to go from a projected angiography/fluoroscopic image to the 3D vessel anatomy. The visualization will help keep focus on the vessels and their environment, potentially increasing efficiency, safety, and lowering the learning curve.

Embodiments described herein are described with respect to the claimed systems as well as with respect to the claimed methods. Features, advantages or alternative embodiments herein can be assigned to the other claimed objects and vice versa. In other words, claims for the systems can be improved with features described or claimed in the context of the methods. In this case, the functional features of the method are embodied by objective units of the providing system.

Furthermore, certain embodiments described herein are described with respect to methods and systems utilizing trained machine learning based networks (or models), as well as with respect to methods and systems for training machine learning based networks. Features, advantages or alternative embodiments herein can be assigned to the other claimed objects and vice versa. In other words, claims for methods and systems for training a machine learning based network can be improved with features described or claimed in context of the methods and systems for utilizing a trained machine learning based network, and vice versa.

In particular, the trained machine learning based networks applied in embodiments described herein can be adapted by the methods and systems for training the machine learning based networks. Furthermore, the input data of the trained machine learning based network can comprise advantageous features and embodiments of the training input data, and vice versa. Furthermore, the output data of the trained machine learning based network can comprise advantageous features and embodiments of the output training data, and vice versa.

In general, a trained machine learning based network mimics cognitive functions that humans associate with other human minds. In particular, by training based on training data, the trained machine learning based network is able to adapt to new circumstances and to detect and extrapolate patterns.

In general, parameters of a machine learning based network can be adapted by means of training. In particular, supervised training, semi-supervised training, unsupervised training, reinforcement learning and/or active learning can be used. Furthermore, representation learning (an alternative term is "feature learning") can be used. In particular, the parameters of the trained machine learning based network can be adapted iteratively by several steps of training.

In particular, a trained machine learning based network can comprise a neural network, a support vector machine, a decision tree, and/or a Bayesian network, and/or the trained machine learning based network can be based on k-means clustering, Q-learning, genetic algorithms, and/or association rules. In particular, a neural network can be a deep neural network, a convolutional neural network, or a convolutional deep neural network. Furthermore, a neural network can be an adversarial network, a deep adversarial network and/or a generative adversarial network.

Figure 8:
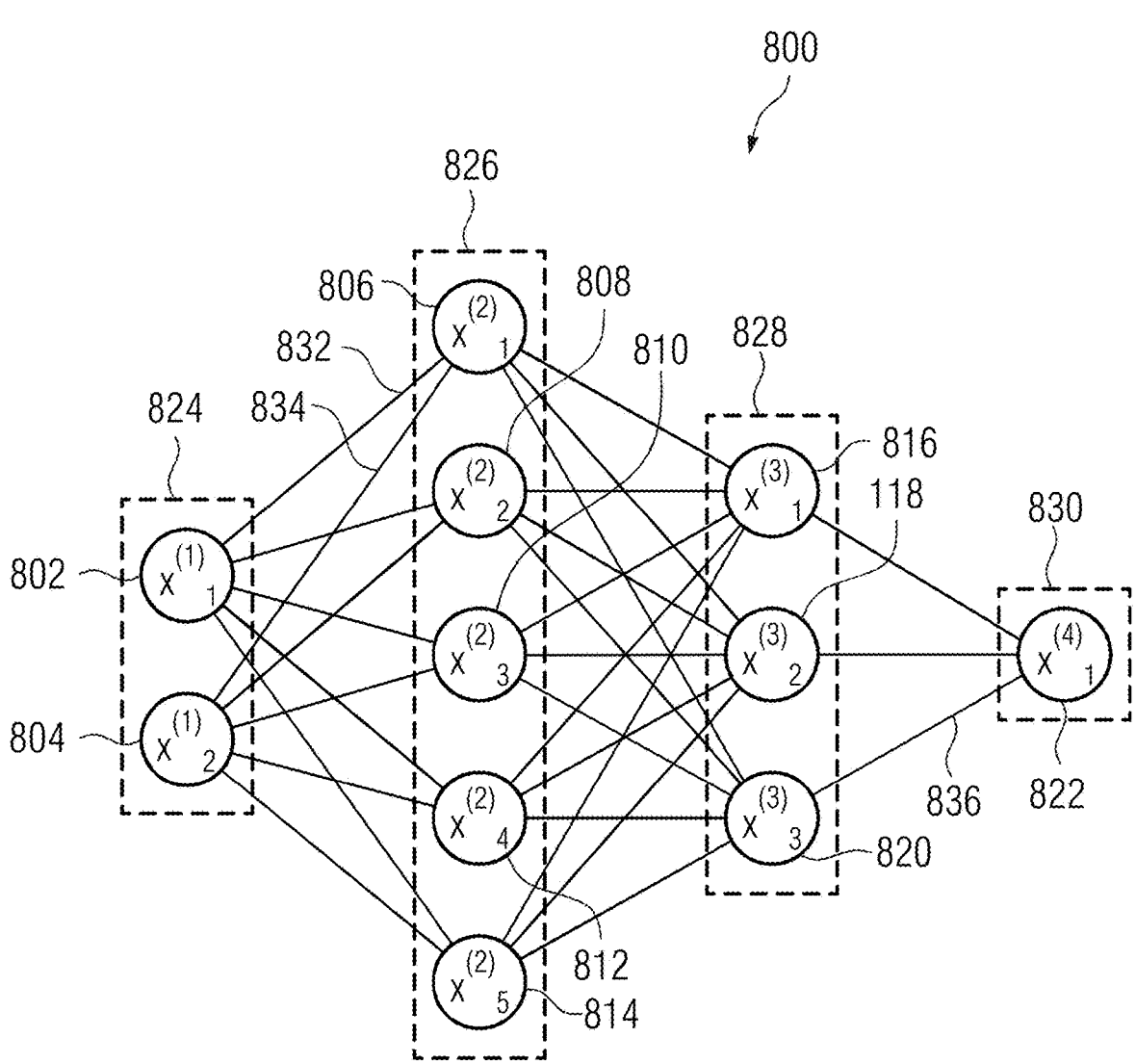
FIG. 8 shows an exemplary artificial neural network that may be used to implement one or more embodiments.

FIG. 8 shows an embodiment of an artificial neural network 800, in accordance with one or more embodiments.

Alternative terms for "artificial neural network" are "neural network", "artificial neural net" or "neural net". Machine learning networks described herein, such as, e.g., the segmentation network utilized to generate CDRM 112, AI agent 120, and the classification network utilized to determine OOD data in FIG. 1, the segmentation network utilized at step 204, the trained AI agent of step 206, and the classification network utilized at step 208 of FIG. 2, segmentation network shown in FIG. 3, and the machine learning network trained according to method 600 of FIG. 6, may be implemented using artificial neural network 800.

The artificial neural network 800 comprises nodes 802-822 and edges 832, 834, . . . , 836, wherein each edge 832, 834, . . . , 836 is a directed connection from a first node 802-822 to a second node 802-822. In general, the first node 802-822 and the second node 802-822 are different nodes 802-822, it is also possible that the first node 802-822 and the second node 802-822 are identical. For example, in FIG. 8, the edge 832 is a directed connection from the node 802 to the node 806, and the edge 834 is a directed connection from the node 804 to the node 806. An edge 832, 834, . . . , 836 from a first node 802-822 to a second node 802-822 is also denoted as "ingoing edge" for the second node 802-822 and as "outgoing edge" for the first node 802-822.

In this embodiment, the nodes 802-822 of the artificial neural network 800 can be arranged in layers 824-830, wherein the layers can comprise an intrinsic order introduced by the edges 832, 834, . . . , 836 between the nodes 802-822. In particular, edges 832, 834, . . . , 836 can exist only between neighboring layers of nodes. In the embodiment shown in FIG. 8, there is an input layer 824 comprising only nodes 802 and 804 without an incoming edge, an output layer 830 comprising only node 822 without outgoing edges, and hidden layers 826, 828 in-between the input layer 824 and the output layer 830. In general, the number of hidden layers 826, 828 can be chosen arbitrarily. The number of nodes 802 and 804 within the input layer 824 usually relates to the number of input values of the neural network 800, and the number of nodes 822 within the output layer 830 usually relates to the number of output values of the neural network 800.

In particular, a (real) number can be assigned as a value to every node 802-822 of the neural network 800. Here, $x^{(n)}_i$ denotes the value of the i-th node 802-822 of the n-th layer 824-830. The values of the nodes 802-822 of the input layer 824 are equivalent to the input values of the neural network 800, the value of the node 822 of the output layer 830 is equivalent to the output value of the neural network 800. Furthermore, each edge 832, 834, . . . , 836 can comprise a weight being a real number, in particular, the weight is a real number within the interval [−1, 1] or within the interval [0, 1]. Here, $w^{(m,n)}_{i,j}$ denotes the weight of the edge between the i-th node 802-822 of the m-th layer 824-830 and the j-th node 802-822 of the n-th layer 824-830. Furthermore, the abbreviation $w^{(n)}_{i,j}$ is defined for the weight $w^{(n,n+1)}_{i,j}$.

In particular, to calculate the output values of the neural network 800, the input values are propagated through the neural network. In particular, the values of the nodes 802-822 of the (n+1)-th layer 824-830 can be calculated based on the values of the nodes 802-822 of the n-th layer 824-830 by $$x^{(n+1)}_j = f\left(\sum_i x^{(n)}_i \cdot w^{(n)}_{i,j}\right).$$

Herein, the function f is a transfer function (another term is "activation function"). Known transfer functions are step functions, sigmoid function (e.g. the logistic function, the generalized logistic function, the hyperbolic tangent, the Arctangent function, the error function, the smoothstep function) or rectifier functions. The transfer function is mainly used for normalization purposes.

In particular, the values are propagated layer-wise through the neural network, wherein values of the input layer 824 are given by the input of the neural network 800, wherein values of the first hidden layer 826 can be calculated based on the values of the input layer 824 of the neural network, wherein values of the second hidden layer 828 can be calculated based in the values of the first hidden layer 826, etc.

In order to set the values $w^{(m,n)}_{i,j}$ for the edges, the neural network 800 has to be trained using training data. In particular, training data comprises training input data and training output data (denoted as $t_i$). For a training step, the neural network 800 is applied to the training input data to generate calculated output data. In particular, the training data and the calculated output data comprise a number of values, said number being equal with the number of nodes of the output layer.

In particular, a comparison between the calculated output data and the training data is used to recursively adapt the weights within the neural network 800 (backpropagation algorithm). In particular, the weights are changed according to $$w'^{(n)}_{i,j} = w^{(n)}_{i,j} - \gamma \cdot \delta^{(n)}_j \cdot x^{(n)}_i$$

wherein $\gamma$ is a learning rate, and the numbers $\delta^{(n)}_j$ can be recursively calculated as $$\delta^{(n)}_j = \left(\sum_k \delta^{(n+1)}_k \cdot w^{(n+1)}_{j,k}\right) \cdot f'\left(\sum_i x^{(n)}_i \cdot w^{(n)}_{i,j}\right)$$

based on $\delta^{(n+1)}_j$, if the (n+1)-th layer is not the output layer, and $$\delta^{(n)}_j = \left(x^{(n+1)}_k - t^{(n+1)}_j\right) \cdot f'\left(\sum_i x^{(n)}_i \cdot w^{(n)}_{i,j}\right)$$

if the (n+1)-th layer is the output layer 830, wherein f' is the first derivative of the activation function, and $y^{(n+1)}_j$ is the comparison training value for the j-th node of the output layer 830.

Figure 9:
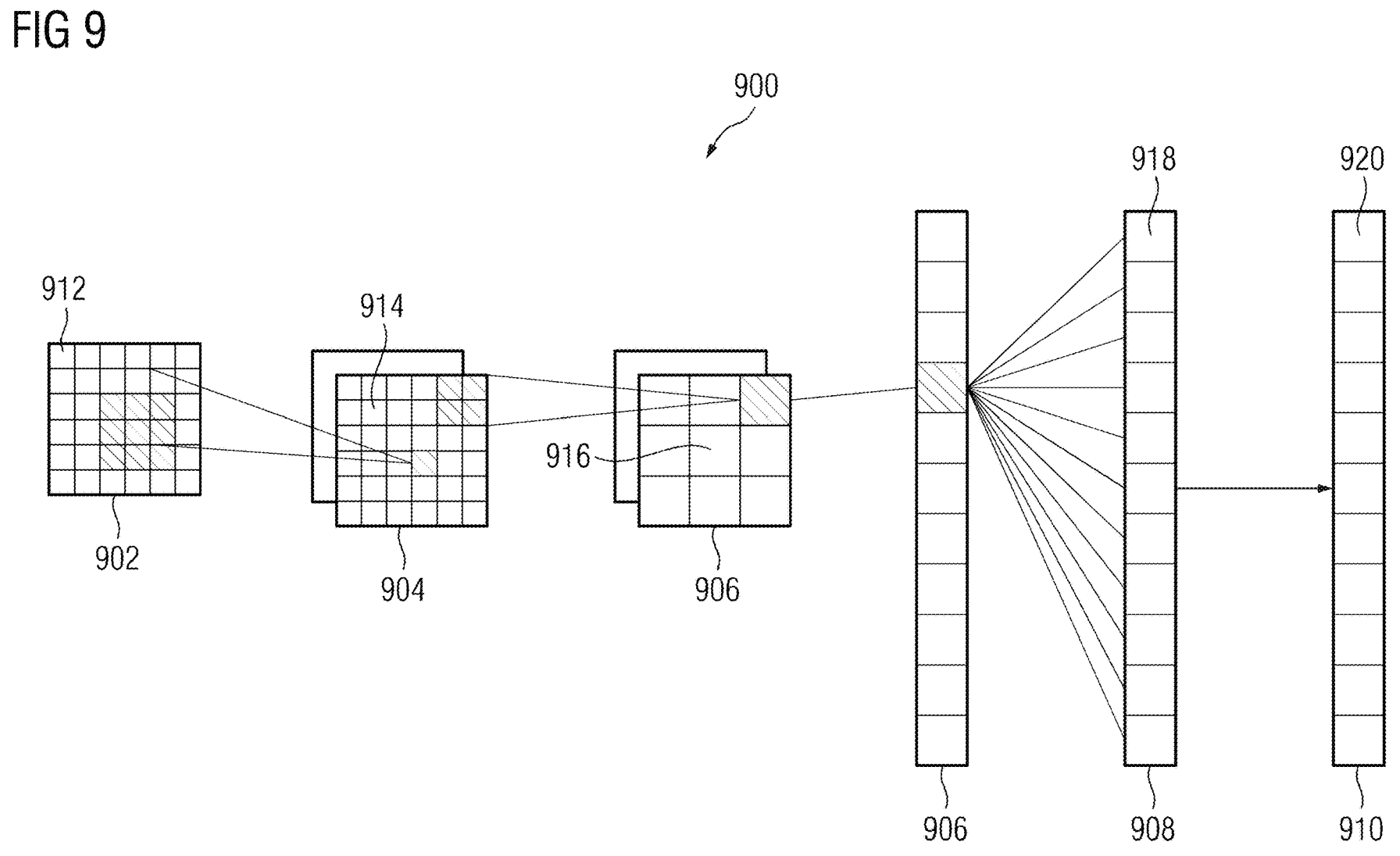

FIG. 9 shows a convolutional neural network 900, in accordance with one or more embodiments. Machine learning networks described herein, such as, e.g., the segmentation network utilized to generate CDRM 112, AI agent 120, and the classification network utilized to determine OOD data in FIG. 1, the segmentation network utilized at step 204, the trained AI agent of step 206, and the classification network utilized at step 208 of FIG. 2, segmentation network shown in FIG. 3, and the machine learning network trained according to method 600 of FIG. 6, may be implemented using convolutional neural network 900.

In the embodiment shown in FIG. 9, the convolutional neural network comprises 900 an input layer 902, a convolutional layer 904, a pooling layer 906, a fully connected layer 908, and an output layer 910. Alternatively, the convolutional neural network 900 can comprise several convolutional layers 904, several pooling layers 906, and several fully connected layers 908, as well as other types of layers.

The order of the layers can be chosen arbitrarily, usually fully connected layers 908 are used as the last layers before the output layer 910.

In particular, within a convolutional neural network 900, the nodes 912-920 of one layer 902-910 can be considered to be arranged as a d-dimensional matrix or as a d-dimensional image. In particular, in the two-dimensional case the value of the node 912-920 indexed with i and j in the n-th layer 902-910 can be denoted as $x^{(n)}_{[i,j]}$. However, the arrangement of the nodes 912-920 of one layer 902-910 does not have an effect on the calculations executed within the convolutional neural network 900 as such, since these are given solely by the structure and the weights of the edges.

In particular, a convolutional layer 904 is characterized by the structure and the weights of the incoming edges forming a convolution operation based on a certain number of kernels. In particular, the structure and the weights of the incoming edges are chosen such that the values $x^{(n)}_k$ of the nodes 914 of the convolutional layer 904 are calculated as a convolution $x^{(n)}_k = K_k * x^{(n-1)}$ based on the values $x^{(n-1)}$ of the nodes 912 of the preceding layer 902, where the convolution * is defined in the two-dimensional case as $$x^{(n)}_k[i, j] = \left(K_k * x^{(n-1)}\right)[i, j] = \sum_{i'} \sum_{j'} K_k[i', j'] \cdot x^{(n-1)}[i - i', j - j'].$$

Here the k-th kernel $K_k$ is a d-dimensional matrix (in this embodiment a two-dimensional matrix), which is usually small compared to the number of nodes 912-918 (e.g. a 3×3 matrix, or a 5×5 matrix). In particular, this implies that the weights of the incoming edges are not independent, but chosen such that they produce said convolution equation. In particular, for a kernel being a 3×3 matrix, there are only 9 independent weights (each entry of the kernel matrix corresponding to one independent weight), irrespectively of the number of nodes 912-920 in the respective layer 902-910. In particular, for a convolutional layer 904, the number of nodes 914 in the convolutional layer is equivalent to the number of nodes 912 in the preceding layer 902 multiplied with the number of kernels.

If the nodes 912 of the preceding layer 902 are arranged as a d-dimensional matrix, using a plurality of kernels can be interpreted as adding a further dimension (denoted as "depth" dimension), so that the nodes 914 of the convolutional layer 904 are arranged as a (d+1)-dimensional matrix. If the nodes 912 of the preceding layer 902 are already arranged as a (d+1)-dimensional matrix comprising a depth dimension, using a plurality of kernels can be interpreted as expanding along the depth dimension, so that the nodes 914 of the convolutional layer 904 are arranged also as a (d+1)-dimensional matrix, wherein the size of the (d+1)-dimensional matrix with respect to the depth dimension is by a factor of the number of kernels larger than in the preceding layer 902.

The advantage of using convolutional layers 904 is that spatially local correlation of the input data can exploited by enforcing a local connectivity pattern between nodes of adjacent layers, in particular by each node being connected to only a small region of the nodes of the preceding layer.

In embodiment shown in FIG. 9, the input layer 902 comprises 36 nodes 912, arranged as a two-dimensional 6×6 matrix. The convolutional layer 904 comprises 72 nodes 914, arranged as two two-dimensional 6×6 matrices, each of the two matrices being the result of a convolution of the values of the input layer with a kernel. Equivalently, the nodes 914 of the convolutional layer 904 can be interpreted as arranges as a three-dimensional 6×6×2 matrix, wherein the last dimension is the depth dimension.

A pooling layer 906 can be characterized by the structure and the weights of the incoming edges and the activation function of its nodes 916 forming a pooling operation based on a non-linear pooling function f. For example, in the two dimensional case the values $x^{(n)}$ of the nodes 916 of the pooling layer 906 can be calculated based on the values $x^{(n-1)}$ of the nodes 914 of the preceding layer 904 as $$x^{(n)}[i, j] = f\left(x^{(n-1)}[id_1, jd_2], \dots, x^{(n-1)}[id_1 + d_1 - 1, jd_2 + d_2 - 1]\right)$$

In other words, by using a pooling layer 906, the number of nodes 914, 916 can be reduced, by replacing a number d1·d2 of neighboring nodes 914 in the preceding layer 904 with a single node 916 being calculated as a function of the values of said number of neighboring nodes in the pooling layer. In particular, the pooling function f can be the max-function, the average or the L2-Norm. In particular, for a pooling layer 906 the weights of the incoming edges are fixed and are not modified by training.

The advantage of using a pooling layer 906 is that the number of nodes 914, 916 and the number of parameters is reduced. This leads to the amount of computation in the network being reduced and to a control of overfitting.

In the embodiment shown in FIG. 9, the pooling layer 906 is a max-pooling, replacing four neighboring nodes with only one node, the value being the maximum of the values of the four neighboring nodes. The max-pooling is applied to each d-dimensional matrix of the previous layer; in this embodiment, the max-pooling is applied to each of the two two-dimensional matrices, reducing the number of nodes from 72 to 18.

A fully-connected layer 908 can be characterized by the fact that a majority, in particular, all edges between nodes 916 of the previous layer 906 and the nodes 918 of the fully-connected layer 908 are present, and wherein the weight of each of the edges can be adjusted individually.

In this embodiment, the nodes 916 of the preceding layer 906 of the fully-connected layer 908 are displayed both as two-dimensional matrices, and additionally as non-related nodes (indicated as a line of nodes, wherein the number of nodes was reduced for a better presentability). In this embodiment, the number of nodes 918 in the fully connected layer 908 is equal to the number of nodes 916 in the preceding layer 906. Alternatively, the number of nodes 916, 918 can differ.

Furthermore, in this embodiment, the values of the nodes 920 of the output layer 910 are determined by applying the Softmax function onto the values of the nodes 918 of the preceding layer 908. By applying the Softmax function, the sum the values of all nodes 920 of the output layer 910 is 1, and all values of all nodes 920 of the output layer are real numbers between 0 and 1.

A convolutional neural network 900 can also comprise a ReLU (rectified linear units) layer or activation layers with non-linear transfer functions. In particular, the number of nodes and the structure of the nodes contained in a ReLU layer is equivalent to the number of nodes and the structure of the nodes contained in the preceding layer. In particular, the value of each node in the ReLU layer is calculated by applying a rectifying function to the value of the corresponding node of the preceding layer.

The input and output of different convolutional neural network blocks can be wired using summation (residual/ dense neural networks), element-wise multiplication (attention) or other differentiable operators. Therefore, the convolutional neural network architecture can be nested rather than being sequential if the whole pipeline is differentiable.

In particular, convolutional neural networks 900 can be trained based on the backpropagation algorithm. For preventing overfitting, methods of regularization can be used, e.g. dropout of nodes 912-920, stochastic pooling, use of artificial data, weight decay based on the L1 or the L2 norm, or max norm constraints. Different loss functions can be combined for training the same neural network to reflect the joint training objectives. A subset of the neural network parameters can be excluded from optimization to retain the weights pretrained on another datasets.

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the steps or functions of the methods and workflows described herein, including one or more of the steps or functions of FIGS. 1-2 and 6. Certain steps or functions of the methods and workflows described herein, including one or more of the steps or functions of FIGS. 1-2 and 6, may be performed by a server or by another processor in a network-based cloud-computing system. Certain steps or functions of the methods and workflows described herein, including one or more of the steps of FIGS. 1-2 and 6, may be performed by a client computer in a network-based cloud computing system. The steps or functions of the methods and workflows described herein, including one or more of the steps of FIGS. 1-2 and 6, may be performed by a server and/or by a client computer in a network-based cloud computing system, in any combination.

Systems, apparatus, and methods described herein may be implemented using a computer program product tangibly embodied in an information carrier, e.g., in a non-transitory machine-readable storage device, for execution by a programmable processor; and the method and workflow steps described herein, including one or more of the steps or functions of FIGS. 1-2 and 6, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 10:
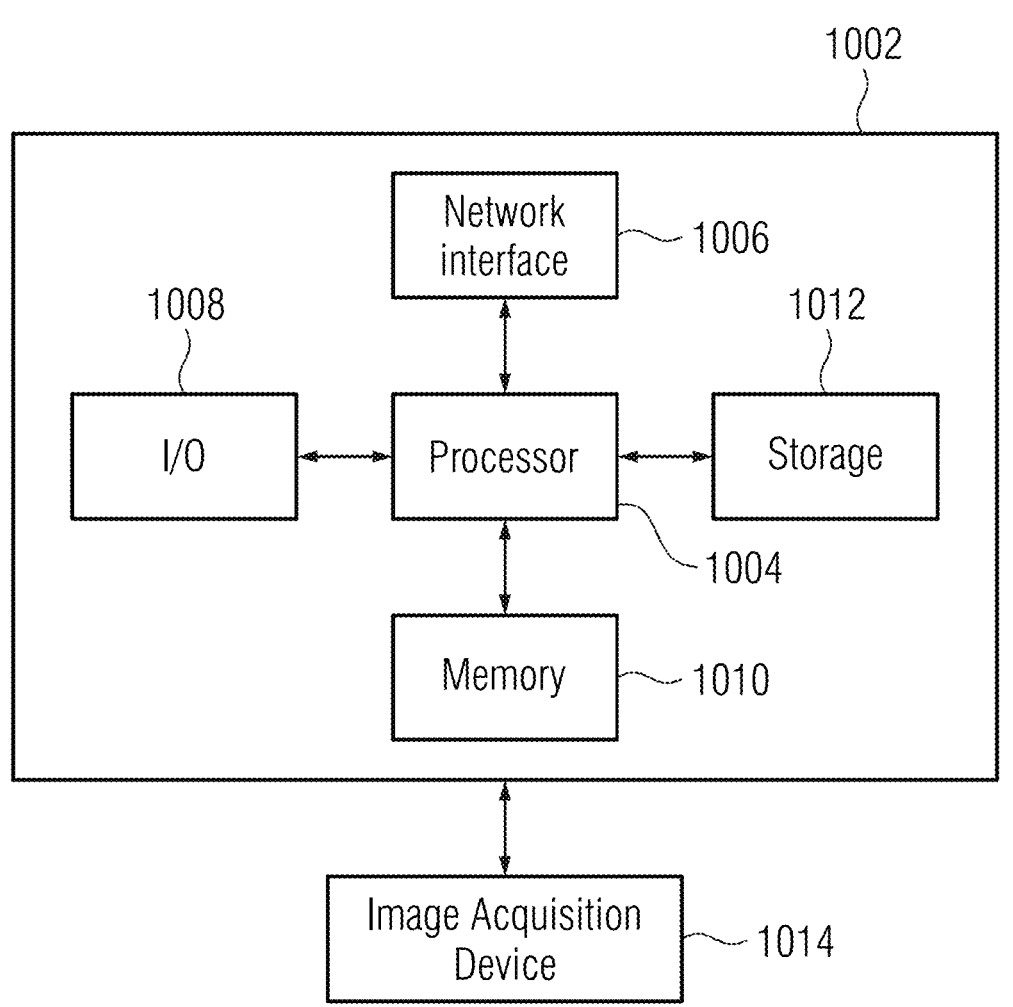
FIG. 10 shows a high-level block diagram of a computer that may be used to implement one or more embodiments.

A high-level block diagram of an example computer 1002 that may be used to implement systems, apparatus, and methods described herein is depicted in FIG. 10. Computer 1002 includes a processor 1004 operatively coupled to a data storage device 1012 and a memory 1010. Processor 1004 controls the overall operation of computer 1002 by executing computer program instructions that define such operations. The computer program instructions may be stored in data storage device 1012, or other computer readable medium, and loaded into memory 1010 when execution of the computer program instructions is desired. Thus, the method and workflow steps or functions of FIGS. 1-2 and 6 can be defined by the computer program instructions stored in memory 1010 and/or data storage device 1012 and controlled by processor 1004 executing the computer program instructions. For example, the computer program instructions can be implemented as computer executable code programmed by one skilled in the art to perform the method and workflow steps or functions of FIGS. 1-2 and 6. Accordingly, by executing the computer program instructions, the processor 1004 executes the method and workflow steps or functions of FIGS. 1-2 and 6. Computer 1002 may also include one or more network interfaces 1006 for communicating with other devices via a network. Computer 1002 may also include one or more input/output devices 1008 that enable user interaction with computer 1002 (e.g., display, keyboard, mouse, speakers, buttons, etc.).

Processor 1004 may include both general and special purpose microprocessors, and may be the sole processor or one of multiple processors of computer 1002. Processor 1004 may include one or more central processing units (CPUs), for example. Processor 1004, data storage device 1012, and/or memory 1010 may include, be supplemented by, or incorporated in, one or more application-specific integrated circuits (ASICs) and/or one or more field programmable gate arrays (FPGAs).

Data storage device 1012 and memory 1010 each include a tangible non-transitory computer readable storage medium. Data storage device 1012, and memory 1010, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 1008 may include peripherals, such as a printer, scanner, display screen, etc. For example, input/output devices 1008 may include a display device such as a cathode ray tube (CRT) or liquid crystal display (LCD) monitor for displaying information to the user, a keyboard, and a pointing device such as a mouse or a trackball by which the user can provide input to computer 1002.

An image acquisition device 1014 can be connected to the computer 1002 to input image data (e.g., medical images) to the computer 1002. It is possible to implement the image acquisition device 1014 and the computer 1002 as one device. It is also possible that the image acquisition device 1014 and the computer 1002 communicate wirelessly through a network. In a possible embodiment, the computer 1002 can be located remotely with respect to the image acquisition device 1014.

Any or all of the systems and apparatus discussed herein may be implemented using one or more computers such as computer 1002.

One skilled in the art will recognize that an implementation of an actual computer or computer system may have other structures and may contain other components as well, and that FIG. 10 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A computer-implemented method comprising:
receiving an input medical image of a patient;
generating a trajectory for navigating a catheter from a current position to a target position in the patient based on the input medical image using a trained segmentation network, wherein the trajectory indicates an uncertainty quantified by the trained segmentation network;
determining, by a trained AI (artificial intelligence) agent and based on the generated trajectory and a current view of the catheter, 1) one or more actions of a robotic navigation system for navigating the catheter from the current position towards the target position and 2) a confidence level associated with the one or more actions;
in response to the confidence level satisfying a threshold, evaluating the one or more actions by determining whether a view of the catheter when navigated according to the one or more actions is out-of-domain of training data on which the trained AI agent is trained; and
navigating the catheter from the current position towards the target position using the robotic navigation system according to the one or more actions based on the evaluation,
wherein the trained segmentation network is trained by:
receiving a set of training images;
training an initial segmentation network based on the set of training images annotated by a single user;

segmenting vessels from a subset of the set of training images using the trained initial segmentation network;
determining a variability distribution for annotations from a plurality of users for the subset of training images based on the segmented vessels;
weighting annotations for the set of training images from certain users of the plurality of users based on the variability distribution;
training a final segmentation network based on the set of training images, the weighted annotations, and an uncertainty associated with each of the weighted annotations; and
outputting the trained final segmentation network.

2. The computer-implemented method of claim 1, wherein generating the trajectory for navigating the catheter from the current position to the target position in the patient based on the input medical image using the trained segmentation network comprises:
generating a colored dynamic roadmap of vessels in the input medical image comprising color coding to indicate the uncertainty quantified by the trained segmentation network.

3. The computer-implemented method of claim 1, further comprising:
in response to the confidence level not satisfying the threshold:
moving the AI agent to a previous position in the trajectory;
optimizing the trajectory for navigating the catheter from the previous position to the target position;
placing the AI agent at a position in the optimal trajectory closest to the current position; and
restarting navigation of the catheter by the AI agent using a view of the catheter at the position in the optimal trajectory closest to the current position as the current view.

4. The computer-implemented method of claim 3, wherein optimizing the trajectory for navigating the catheter from the previous position to the target position comprises:
optimizing the trajectory based on possible actions of the robotic navigation system and a segmentation of vessels in from the input medical image.

5. The computer-implemented method of claim 1, wherein evaluating the one or more actions comprises:
evaluating a bending stress and a number of punctures of a guidewire for navigating the catheter.

6. The computer-implemented method of claim 1, further comprising:
storing a configuration of the robotic navigation system while a user performs a set of actions navigating the catheter; and
replaying the set of actions based on the stored configuration of the robotic navigation system.

7. The computer-implemented method of claim 1, further comprising:
receiving user input of a selection of a position at which the catheter is to navigate;
computing kinematics for navigating the catheter to the selected position; and
navigating the catheter to the selected position based on the computed kinematics.

8. The computer-implemented method of claim 1, further comprising:
computing a safety margin for a path in the input medical image; and providing haptic feedback to a user navigating the catheter based on a current position of the catheter with respect to the safety margin.

9. An apparatus comprising:

means for receiving an input medical image of a patient;

means for generating a trajectory for navigating a catheter from a current position to a target position in the patient based on the input medical image using a trained segmentation network, wherein the trajectory indicates an uncertainty quantified by the trained segmentation network;

means for determining, by a trained AI (artificial intelligence) agent and based on the generated trajectory and a current view of the catheter, 1) one or more actions of a robotic navigation system for navigating the catheter from the current position towards the target position and 2) a confidence level associated with the one or more actions;

means for, in response to the confidence level satisfying a threshold, evaluating the one or more actions by determining whether a view of the catheter when navigated according to the one or more actions is out-of-domain of training data on which the trained AI agent is trained; and means for navigating the catheter from the current position towards the target position using the robotic navigation system according to the one or more actions based on the evaluation, wherein the trained segmentation network is trained by:

receiving a set of training images;

training an initial segmentation network based on the set of training images annotated by a single user;

segmenting vessels from a subset of the set of training images using the trained initial segmentation network;

determining a variability distribution for annotations from a plurality of users for the subset of training images based on the segmented vessels;

weighting annotations for the set of training images from certain users of the plurality of users based on the variability distribution;

training a final segmentation network based on the set of training images, the weighted annotations, and an uncertainty associated with each of the weighted annotations; and outputting the trained final segmentation network.

10. The apparatus of claim 9, wherein the means for generating the trajectory for navigating the catheter from the current position to the target position in the patient based on the input medical image using the trained segmentation network comprises:

means for generating a colored dynamic roadmap of vessels in the input medical image comprising color coding to indicate the uncertainty quantified by the trained segmentation network.

11. The apparatus of claim 9, further comprising:

in response to the confidence level not satisfying the threshold:

means for moving the AI agent to a previous position in the trajectory;

means for optimizing the trajectory for navigating the catheter from the previous position to the target position;

means for placing the AI agent at a position in the optimal trajectory closest to the current position; and means for restarting navigation of the catheter by the AI agent using a view of the catheter at the position in the optimal trajectory closest to the current position as the current view.

12. The apparatus of claim 11, wherein the means for optimizing the trajectory for navigating the catheter from the previous position to the target position comprises:

means for optimizing the trajectory based on possible actions of the robotic navigation system and a segmentation of vessels in from the input medical image.

13. The apparatus of claim 9, wherein the means for evaluating the one or more actions comprises:

means for evaluating a bending stress and a number of punctures of a guidewire for navigating the catheter.

14. The apparatus of claim 9, further comprising:

means for storing a configuration of the robotic navigation system while a user performs a set of actions navigating the catheter; and means for replaying the set of actions based on the stored configuration of the robotic navigation system.

15. A non-transitory computer readable medium storing computer program instructions, the computer program instructions when executed by a processor cause the processor to perform operations comprising:

receiving an input medical image of a patient;

generating a trajectory for navigating a catheter from a current position to a target position in the patient based on the input medical image using a trained segmentation network, wherein the trajectory indicates an uncertainty quantified by the trained segmentation network;

determining, by a trained AI (artificial intelligence) agent and based on the generated trajectory and a current view of the catheter, 1) one or more actions of a robotic navigation system for navigating the catheter from the current position towards the target position and 2) a confidence level associated with the one or more actions;

in response to the confidence level satisfying a threshold, evaluating the one or more actions by determining whether a view of the catheter when navigated according to the one or more actions is out-of-domain of training data on which the trained AI agent is trained; and navigating the catheter from the current position towards the target position using the robotic navigation system according to the one or more actions based on the evaluation, wherein the trained segmentation network is trained by:

receiving a set of training images;

training an initial segmentation network based on the set of training images annotated by a single user;

segmenting vessels from a subset of the set of training images using the trained initial segmentation network;

determining a variability distribution for annotations from a plurality of users for the subset of training images based on the segmented vessels;

weighting annotations for the set of training images from certain users of the plurality of users based on the variability distribution;

training a final segmentation network based on the set of training images, the weighted annotations, and an uncertainty associated with each of the weighted annotations; and outputting the trained final segmentation network.

16. The non-transitory computer readable medium of claim 15, wherein generating the trajectory for navigating the catheter from the current position to the target position in the patient based on the input medical image using the trained segmentation network comprises:

generating a colored dynamic roadmap of vessels in the input medical image comprising color coding to indicate the uncertainty quantified by the trained segmentation network.

17. The non-transitory computer readable medium of claim 15, the operations further comprising:

in response to the confidence level not satisfying the threshold:

moving the AI agent to a previous position in the trajectory;

optimizing the trajectory for navigating the catheter from the previous position to the target position;

placing the AI agent at a position in the optimal trajectory closest to the current position; and restarting navigation of the catheter by the AI agent using a view of the catheter at the position in the optimal trajectory closest to the current position as the current view.

18. The non-transitory computer readable medium of claim 15, wherein evaluating the one or more actions comprises:

evaluating a bending stress and a number of punctures of a guidewire for navigating the catheter.

19. The non-transitory computer readable medium of claim 15, the operations further comprising:

receiving user input of a selection of a position at which the catheter is to navigate;

computing kinematics for navigating the catheter to the selected position; and navigating the catheter to the selected position based on the computed kinematics.

20. The non-transitory computer readable medium of claim 15, the operations further comprising:

computing a safety margin for a path in the input medical image; and providing haptic feedback to a user navigating the catheter based on a current position of the catheter with respect to the safety margin.

\* \* \* \* \*